United States Patent [19]

Rosenthal et al.

[11] Patent Number: 5,438,201
[45] Date of Patent: Aug. 1, 1995

[54] METHOD AND APPARATUS FOR RESTRAINING FINGER MOTION IN BLOOD ANALYTE OPTICAL MEASUREMENT

[75] Inventors: Robert D. Rosenthal, Gaithersburg, Md.; Ryoichi Yabe, Tokyo, Japan

[73] Assignee: Futrex, Inc., Gaithersburg, Md.

[21] Appl. No.: 195,654

[22] Filed: Feb. 15, 1994

Related U.S. Application Data

[63] Continuation-in-part of Ser. No. 103,758, Aug. 10, 1993, Pat. No. 5,362,966, which is a continuation-in-part of Ser. No. 813,739, Dec. 30, 1991, Pat. No. 5,237,178, which is a continuation-in-part of Ser. No. 565,302, Aug. 10, 1990, Pat. No. 5,077,476, which is a continuation-in-part of Ser. No. 544,580, Jun. 27, 1990, Pat. No. 5,086,229.

[51] Int. Cl.⁶ .......................................... G01N 21/35
[52] U.S. Cl. .................................. 250/341.1; 128/664
[58] Field of Search .................... 250/341.1, 340, 343, 250/339.06, 339.07, 339.12; 128/633, 664, 666, 665, 687

[56] References Cited

U.S. PATENT DOCUMENTS

| | | | |
|---|---|---|---|
| 3,463,142 | 8/1969 | Harte . | |
| 4,442,844 | 4/1984 | Navach | 128/664 |
| 5,125,403 | 6/1992 | Culp | 128/633 |
| 5,159,929 | 11/1992 | Morris et al. . | |
| 5,209,230 | 5/1993 | Swedlow et al. . | |
| 5,217,012 | 6/1993 | Young et al. | 128/633 |

OTHER PUBLICATIONS

Robinson et al., *Clin. Chem.*, 38/9, 1618–1622 (1992).
Rosenthal et al., "Investigation of Non-Invasive Measurement of Blood Glucose", presented at the International Diabetes Federation Congress in Washington, D.C. (Jun. 24, 1991).

*Primary Examiner*—P. M. Dzierzynski
*Assistant Examiner*—Richard Hanig
*Attorney, Agent, or Firm*—Rothwell, Figg, Ernst & Kurz

[57] ABSTRACT

A method and apparatus for preventing undesirable index finger rotational motion within a non-invasive quantitative blood analyte measurement instrument includes placing at least the middle finger or the thumb into proper alignment with the index finger when inserted in the instrument to prevent the index finger from rotating with respect to the instrument's optical axis. The natural pincer-type relationship of the thumb and index finger is used to align the index finger in the optical axis by the positioning of the thumb and the positioning of the middle finger is used to hinder the rotation of the finger toward the thumb away from the optical axis. Conductive material is provided in grooves formed on the instrument housing to dissipate EMI energy from the test subject.

9 Claims, 3 Drawing Sheets

METHOD AND APPARATUS FOR RESTRAINING FINGER MOTION IN BLOOD ANALYTE OPTICAL MEASUREMENT

CROSS-REFERENCE TO RELATED APPLICATIONS

This application is a continuation-in-part of application Ser. No. 08/103,758, filed Aug. 10, 1993, now U.S. Pat. No. 5,362,966 which is a continuation-in-part of Ser. No. 07/813,739, filed Dec. 30, 1991 and now U.S. Pat. No. 5,237,178, which is a continuation-in-part of Ser. No. 07/565,302, filed Aug. 10, 1990, now U.S. Pat. No. 5,077,476, which is a continuation-in-part of application Ser. No. 07/544,580, filed Jun. 27, 1990, now U.S. Pat. No. 5,086,229.

BACKGROUND OF THE INVENTION

1. Field of the Invention

This invention relates to instruments for the noninvasive quantitative measurement of constituents in blood, such as blood glucose levels. Specifically, this invention relates to an improved analysis instrument which achieves improved accuracy in measurement by ensuring that the position of the subject's finger in the instrument remains constant each time the finger is inserted into the instrument.

2. Description of the Background Art

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

A current type of blood glucose analytical instrumentation is available for the specific purpose of determining blood glucose levels in people with diabetes. This technology uses a small blood sample from a finger poke which is placed on a chemically treated carrier and is inserted into a portable battery operated instrument. The instrument analyzes the blood sample and provides a blood glucose level reading in a short period of time.

A different class of blood glucose analytical instruments is the near-infrared quantitative analysis instrument which noninvasively measures blood glucose, such as the type described in U.S. Pat. No. 5,077,476, incorporated by reference herein. The noninvasive blood glucose measurement instrument analyzes near-infrared energy following interactance with venous or arterial blood, or transmission through a blood-containing body part. The instrument measures a change in light absorption that occurs, in part, due to the glucose content of the blood stream.

Non-invasive measurement instruments of this type have broad applications for the diabetic community. For example, people with diabetes have wide changes in their blood glucose content during the day which often require multiple measurements per day for good disease control. The ability to make these near-infrared blood glucose level measurements noninvasively means that more measurements will likely be made per day than would be made using the more painful blood drawing approach.

An example of a non-invasive measurement instrument is disclosed in U.S. Pat. No. 5,086,229, also incorporated by reference herein, wherein an individual user places the most distal portion of his or her finger within a "jaws" type arrangement. Near-infrared energy within the spectrum of interest is then impinged upon the surface of the finger and a detector is placed axially with the near-infrared beam on the opposite side of the finger to receive any near-infrared energy emerging therefrom. A microprocessor receives the amplified signal from the detector and calculates the user's blood glucose level. The near-infrared energy is within a bandwidth of 600–1100 nm, and preferably 600–1000 nm.

Data obtained from experimentation has revealed that the accuracy of such non-invasive measurement of a blood analyte such as glucose is dependent upon the repeatability of proper finger positioning within the instrument. In particular, the inserted finger must be consistently aligned with the optical axis of the instrument. The light path of the near-infrared light source should preferably pass through the center of the cuticle to obtain high accuracy measurements. Thus, it is desirable to avoid rotation of the finger once inserted into the instrument.

There is a natural tendency when grasping an object for the index finger and thumb to form a pincer-type relationship in which the index finger is slightly rotated with respect to the other fingers so that the finger pad on the bottom side of the index finger faces the pad on the bottom side of the thumb.

FIG. 1 illustrates a typical near-infrared measurement apparatus 10 for non-invasive optical measurement of blood analytes. The apparatus has an aperture (not visible) for insertion of the index finger of the hand 20 of a subject into the optical path of the light source between the light source and detector. In this design, the left index finger is inserted into the aperture of the unit with the thumb on one side of the unit and the other three fingers on the other side of the unit. As such, the index finger tends to rotate upon insertion to form a pincer-type relationship with the thumb. Dependent on the particular positioning of the thumb and the other three fingers on the unit during any one insertion, the index finger will assume a different rotational placement within the light path of the instrument.

SUMMARY OF THE INVENTION

The present invention solves the problems associated with index finger rotation in the conventional apparatus to ensure that the index finger always maintains a consistent positional relationship with the light path of the instrument. As a result, repeatable accuracy of quantitative blood analyte measurements is improved.

In particular, the present invention provides a method of restraining index finger rotational motion in an optical quantitative measurement apparatus, comprising the step of causing at least one other finger of the subject to be aligned with the index finger after the index finger has been inserted into the aperture of the instrument, whereby the index finger is prevented from rotating within the aperture to enable the instrument to provide accurate repeatable quantitative measurements.

The present invention further provides an optical quantitative measurement apparatus having an aperture for insertion of the index finger of a subject, wherein quantitative measurement of blood analytes is performed by irradiating said index finger with radiation in a predetermined bandwidth, comprising a housing and alignment means provided on the housing for aligning at least one other finger of the subject with the index finger after the index finger has been inserted into the aperture, whereby the index finger is prevented from rotating within the aperture to thereby enable the apparatus to provide accurate repeatable quantitative measurements.

BRIEF DESCRIPTION OF THE DRAWINGS

These and other advantages of the present invention will become more fully understood from the following detailed description in conjunction with the accompanying drawings, which are provided by way of illustration only and thus are not limitative of the present invention, and wherein.

DETAILED DESCRIPTION OF THE PREFERRED EMBODIMENTS

Two alternate methods are provided by the present invention for ensuring that the index finger once inserted into the instrument always maintains a constant positional relationship with the light path within the unit. These two methods can be used individually or in combination, and preferably are used in combination to achieve the highest level of positioning accuracy.

Figure 1:
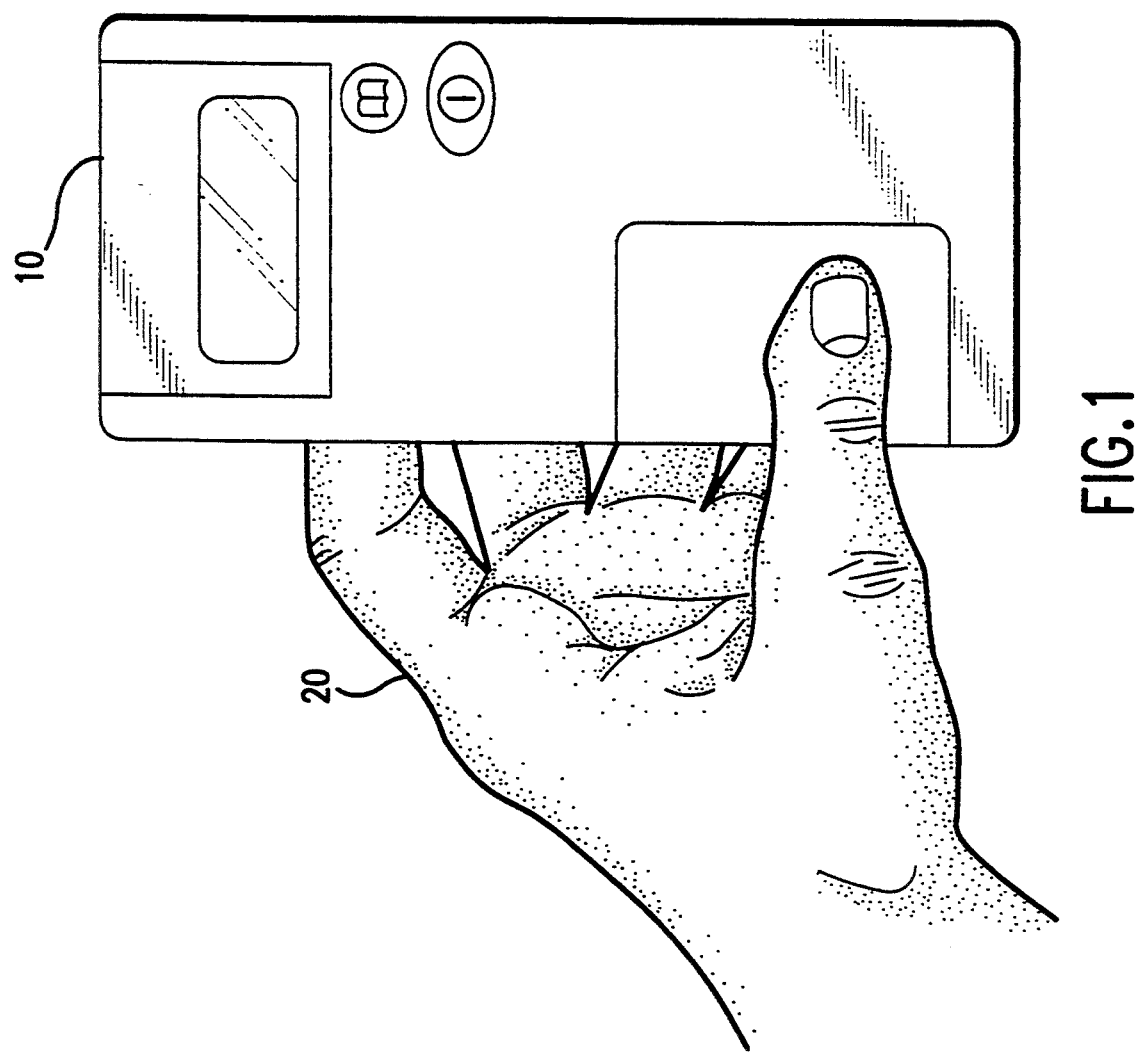
FIG. 1 is a plan view of a conventional noninvasive instrument for quantitative measurement of blood analytes.
Figure 2:
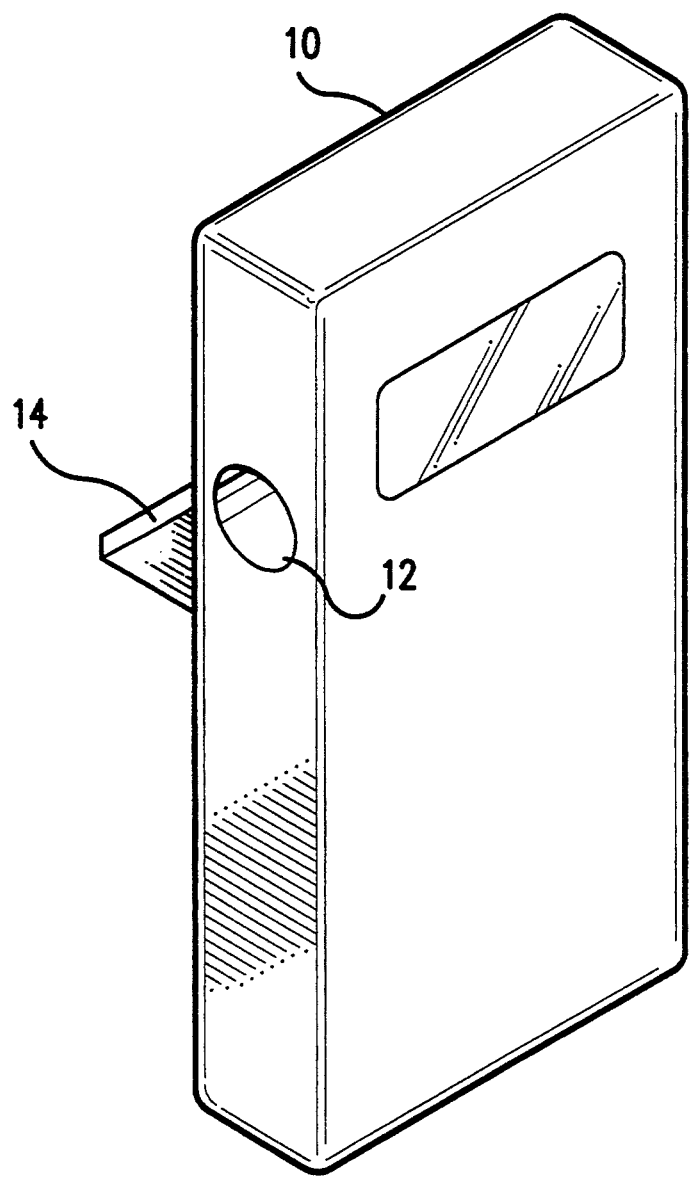
FIG. 2 is a perspective view of one preferred embodiment of the present invention.

Referring to FIG. 2, a finger shelf 14 is provided on one side of the unit 10 for placement of the middle finger when the index finger is inserted into aperture 12. The shelf 14 is provided on the left side of the unit when the left hand index finger is used to take the measurement (i.e., for right-handed persons), and correspondingly, the shelf 14 can be equivalently located on the right side of units designed for left-handed persons. Placement of the middle finger on the shelf 14 forces the index finger to remain rotationally centered within the light path of the instrument and prevents the index finger from following the tendency to rotate toward the thumb to a pincer-type relationship. The shelf 14 should be located so that the middle finger rests at a height equal to or slightly above the center line of the index finger when inserted into the instrument. In this way, the index finger assumes the same orientation as the middle finger, allowing the center of the cuticle to remain in the light path. Instead of a shelf, a groove may be equivalently provided in the body of the unit for placement of the middle finger.

Figure 3:
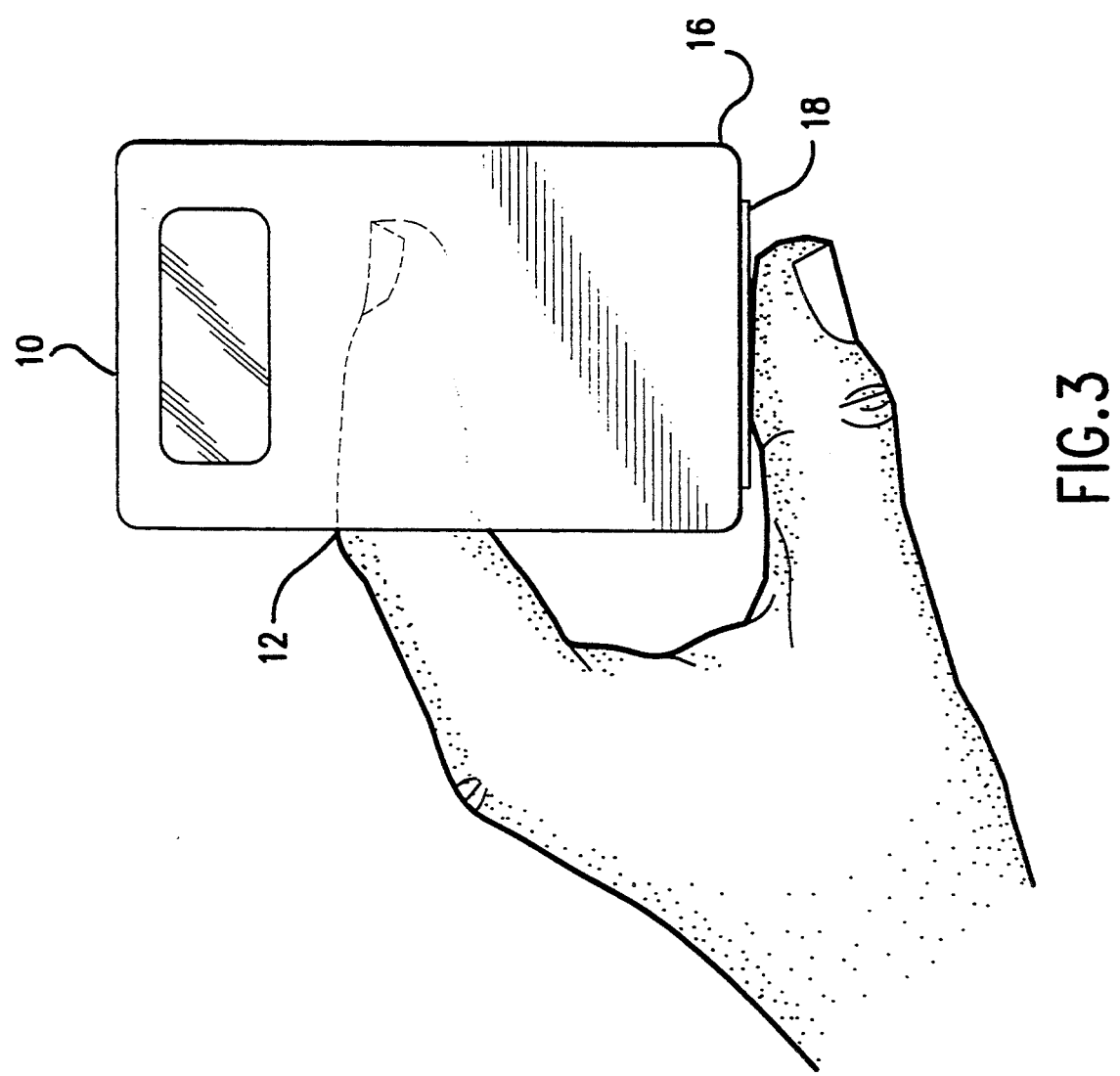
FIG. 3 is a plan view of another preferred embodiment of the present invention.

A second embodiment of the invention is shown in FIG. 3, wherein the thumb is placed on the bottom edge 16 of the unit 10 in vertical alignment with the index finger inserted in the aperture 12 and with the optical axis of the measuring components. This positional relationship between the index finger and thumb utilizes the natural tendency toward the pincer formation to ensure that the index finger is properly aligned with the optical axis. In a preferred embodiment, a groove can be formed in the bottom edge 16 for guiding the thumb into the proper location.

Preferably, the instrument is designed to have two grooves in the housing: the first being located on the side of the instrument at an elevation at least equal to the insertion aperture for the index finger or slightly higher, to provide a resting location for the middle finger; and the second being groove being located on the bottom edge of the instrument for guiding the thumb under the index finger in the plane of the optical axis of the equipment. In such manner the index finger is repeatably positioned within the instrument at a constant orientation, preventing rotation and ensuring repeatable measurements of high accuracy.

The present invention further provides elimination of electromagnetic interference (EMI) from the measurement process. EMI can be a major problem because the human body acts as an antenna with respect to the absorption of radio and other energy waves throughout the electromagnetic spectrum. These waves interfere with the proper functioning of the detector in the unit because the detector will receive not only the optical energy from the light source but also the transient and unpredictable EMI energy, and therefore can cause significant measurement errors. EMI is eliminated in the present invention by providing a grounding plate 18 made of conductive material within the groove located on the bottom 16 of the unit, or also within the groove on the side of the unit. The conductive material is connected to the grounding of the electronics within the instrument. When the finger or thumb is in contact with the conductive material, EMI energy is dissipated through the grounding plate 18 and does not interfere with the operation of the detector.

The invention having been described, it will be apparent to those skilled in the art that the same may varied in many ways without departing from the spirit and scope of the invention. Consequently, any and all such variations are intended to be included within the scope of the following claims.

What is claimed is:

1. In an optical quantitative measurement apparatus having an aperture for insertion of the index finger of a subject, wherein quantitative measurement of blood analytes is performed by irradiating said index finger with radiation in a predetermined bandwidth, a method of restraining index finger rotational motion comprising the step of:

causing the middle finger of the subject to be aligned with said index finger after said index finger has been inserted into said aperture by providing means for aligning the middle finger of said subject in a horizontal place at least as high as a horizontal plane of said index finger;

whereby said index finger is prevented from rotating within said aperture to enable said apparatus to provide accurate repeatable quantitative measurements.

2. A method of restraining index finger rotational motion as set forth in claim 1, wherein said causing step comprises the step of providing means for aligning the thumb of said subject in the same vertical plane as said index finger.

3. A method of restraining index finger rotational motion as set forth in claim 2, wherein said causing step further comprises the step of providing means for aligning the middle finger of said subject in a horizontal plane at least as high as a horizontal plane of said index finger.

4. A method of restraining index finger rotational motion as set forth in claim 2, wherein said means for aligning the thumb of said subject comprises a groove formed in the bottom surface of said apparatus into which said thumb is placed, further comprising the step of providing conductive material in said groove connected to ground potential, wherein placement of said thumb in said groove causes said subject to be grounded.

5. An optical quantitative measurement apparatus having an aperture for insertion of the index finger of a subject, wherein quantitative measurement of blood analytes is performed by irradiating said index finger with radiation in a predetermined bandwidth, comprising:
- a housing; and
- alignment means provided on said housing for aligning at least one other finger of the subject with said index finger after said index finger has been inserted into said aperture;
- whereby said index finger is prevented from rotating within said aperture to enable said apparatus to provide accurate repeatable quantitative measurements.

6. An optical quantitative measurement apparatus as set forth in claim 5, wherein said alignment means comprises means for aligning the middle finger of said subject in a horizontal plane at least as high as a horizontal plane of said index finger.

7. An optical quantitative measurement apparatus as set forth in claim 5, wherein said alignment means comprises means for aligning the thumb of said subject in the same vertical plane as said index finger.

8. An optical quantitative measurement apparatus as set forth in claim 7, wherein said alignment means further comprises means for aligning the middle finger of said subject in a horizontal plane at least as high as a horizontal plane of said index finger.

9. An optical quantitative measurement apparatus as set forth in claim 7, wherein said means for aligning the thumb of said subject comprises a groove formed in the bottom surface of said apparatus into which said thumb is placed, a surface of said groove contacting said thumb comprising conductive material connected to ground potential, whereby placement of said thumb in said groove causes said subject to be grounded.

* * * * *